US012544056B2

(12) United States Patent
Romelli et al.

(10) Patent No.: US 12,544,056 B2
(45) Date of Patent: Feb. 10, 2026

(54) SURGICAL SPACE MAKER DEVICE

(71) Applicant: AtriCure, Inc., Mason, OH (US)

(72) Inventors: Jackson Thomas Romelli, Cincinnati, OH (US); Matthew V. Monti, Cincinnati, OH (US)

(73) Assignee: AtriCure, Inc., Mason, OH (US)

(*) Notice: Subject to any disclaimer, the term of this patent is extended or adjusted under 35 U.S.C. 154(b) by 164 days.

(21) Appl. No.: 18/487,951

(22) Filed: Oct. 16, 2023

(65) Prior Publication Data

US 2024/0122589 A1 Apr. 18, 2024

Related U.S. Application Data

(60) Provisional application No. 63/379,517, filed on Oct. 14, 2022.

(51) Int. Cl.
*A61B 17/02* (2006.01)

(52) U.S. Cl.
CPC ................................ *A61B 17/0218* (2013.01)

(58) Field of Classification Search
CPC ................................................. A61B 17/0218
USPC ........................... 600/201-245; 606/190-194
See application file for complete search history.

(56) References Cited

U.S. PATENT DOCUMENTS

| | | | | |
|---|---|---|---|---|
| 5,275,610 | A * | 1/1994 | Eberbach | A61B 17/0218 606/198 |
| 5,309,896 | A | 5/1994 | Moll et al. | |
| 5,402,772 | A | 4/1995 | Moll et al. | |
| 6,890,295 | B2 | 5/2005 | Michels et al. | |
| 9,592,042 | B2 | 3/2017 | Titus | |
| 9,883,867 | B2 | 2/2018 | Martin et al. | |
| 10,933,222 | B2 | 3/2021 | Weitzner et al. | |
| 11,000,289 | B2 | 5/2021 | Miles et al. | |
| 2015/0223795 | A1* | 8/2015 | Mariani | A61B 17/0218 600/204 |
| 2020/0352431 | A1 | 11/2020 | Piskun | |
| 2021/0177244 | A1* | 6/2021 | Weitzner | A61B 1/00066 |

* cited by examiner

*Primary Examiner* — Julianna N Harvey
*Assistant Examiner* — Tara Rose E Carter
(74) *Attorney, Agent, or Firm* — Levine Bagade Han LLP

(57) ABSTRACT

A surgical space maker device has a flexible member comprising an expandable space-making frame where at least a first frame member and a second frame member of the space-making frame are axially advanceable relative to each other.

24 Claims, 13 Drawing Sheets

SURGICAL SPACE MAKER DEVICE

CROSS-REFERENCE TO RELATED APPLICATIONS

This application is a non-provisional application of U.S. Provisional Application No. 63/397,517 filed Oct. 14, 2022, the entirety of which is incorporated by reference.

FIELD OF THE INVENTION

The present application is directed to surgical instruments having an expandable distal section that is configured to reposition surrounding tissue. The present disclosure is also directed to medical instruments, methods, and devices for creating space adjacent to areas of interest on tissues, organs, and other body structures, which permit increased visualization of the area by the surgical operator as well as increased access to the area allowing the use of various medical devices.

BACKGROUND OF THE INVENTION

Devices for accessing and visualizing interior regions of a body cavity are known. Typically, such devices use an inflatable balloon or an expandable hood, which is typically introduced over the region of interest and then expanded or opened over the tissue region of interest.

However, the use of such devices is not optimal and can present inherent disadvantages. For instance, balloons are typically inflated to a relatively large size and to a pressure that may undesirably displace surrounding tissue and interfere with access to the region of interest. The use of hoods also limits access to the region of tissue within the interior area of the hood.

There remains a need for a space-making device that creates an access space adjacent to a region of interest while maximizing access to the tissues in and around the region of interest while providing the operator to select the size and orientation of the device to produce an access space that is best suited for the local anatomy and procedure.

SUMMARY OF THE INVENTION

The present disclosure includes surgical space-making devices for separating anatomic structures to permit the use of a medical device at a region of interest. In one variation, a surgical space-making device includes a handle having a first actuator and a second actuator each independently operational; a shaft extending distally along an axis from the handle, the shaft having an interior lumen; a working end at a distal end of the shaft where the interior lumen is open at the working end; a space-making frame located at the working end, the space-making frame comprising an arcuate frame member moveable by operation of the first actuator and a secondary frame member moveable by operation of the second actuator, where the arcuate frame member and secondary frame member are coupled together; wherein operation of the first actuator and operation of the second actuator to move the arcuate frame member and the secondary frame member in a same direction causes the space-making frame to move axially relative to the working end; and wherein operation of the first actuator and operation of the second actuator to move the arcuate frame member and the secondary frame member relative to each other causes the space-making frame to expand away from the axis to an expanded profile permitting separation of anatomic structures adjacent to the working end to create a space adjacent to the region of interest such that the medical device can be advanced through the interior lumen towards the region of interest.

In another variation, a surgical space-making device can include a handle having a first actuator and a second actuator, the first actuator and the second actuator independently operable relative to each other; a shaft extending distally from the handle along an axis, the shaft having an interior lumen; a working end at a distal end of the shaft where the interior lumen is open at the working end; a space-making frame located at the working end, the space-making frame comprising a first arcuate frame member and a secondary frame member; the first arcuate frame member comprising a first strut and a second strut and a mid-portion, where the first strut and the second strut are spaced apart at the working end and are mechanically coupled to the first actuator such that operation of the first actuator causes axial movement of the first arcuate frame member relative to the working end; the secondary frame member having a first leg having a distal segment coupled to the mid-portion of the first arcuate frame member, a proximal segment of the secondary frame member coupled to the second actuator such that operation of the second actuator causes axial movement of the secondary frame member relative to the working end; wherein operation of the first actuator and the second actuator to move the first arcuate frame member and the secondary frame member in a single direction causes an axial movement of the space-making frame relative to the working end; and wherein operation of the first actuator and the second actuator to move the first arcuate frame member and the secondary frame member relative to each other causes the space-making frame to expand away in a radial direction from the axis of shaft to cause separation of tissue adjacent to the working end and creating a space at the region of interest such that the medical device can be advanced through the interior lumen to the region of interest.

Variations of the device include a space-making frame that is compliant such that an anatomical movement of an organ causes the space-making frame to deflect.

In additional variations, the secondary frame member comprises a secondary arcuate frame member. Alternatively, the secondary frame member can comprise a single strut.

The cross-sections of the frame members can comprise a cross-section selected from the group consisting of a circular shape, a non-symmetrical shape, a shape having irregular surfaces, a square shape, an oval shape, a rectangular shape, and a combination thereof.

The actuators of the surgical space-making devices can be rotary actuators or linear actuators.

In another variation, one of the actuators is spring-biased into a locking position. This spring bias can be provided by a spring member or by a portion of the arcuate frame member.

The surgical space-making device described herein can include a space-making frame configured to expand asymmetrically about the axis upon selective advancement of the arcuate frame member and the secondary frame member.

Variations of the surgical space-making device can optionally include an interior lumen. In those variations that include a lumen, the lumen is sized to allow the advancement of one or more medical instruments therethrough.

The present disclosure also includes methods of creating a space adjacent to an anatomic structure to create a space for the use of a medical device adjacent to a region of interest. For example, such methods can include positioning a shaft of a space-making device adjacent the anatomic structure such that a space-making frame at a distal region of the shaft is adjacent to the region of interest, where the shaft comprises a working channel extending along an axis and where the space-making frame comprises a first arcuate frame member and a secondary frame member coupled together at a distal portion; operating a first actuator to cause axial movement of the first arcuate frame member relative to the secondary frame member, where the secondary frame member alters a shape of the first arcuate frame member resulting in expansion of the space-making frame away from the axis of the working channel to separate the anatomic structure from another anatomic structure to create the space; and advancing the medical device through the working channel into the space.

The method can further include operating the second actuator independently of the first actuator to alter the shape of the space-making frame. In additional variations, the space-making frame is compliant such that expansion of the space-making frame against an organ does not affect an output of the organ.

The space-making frames described herein can comprise a wire-frame structure that permits separation of tissues but also maximizes the ability to access tissues adjacent to the structure.

In one or more aspects of the present disclosure, another variation of a surgical space maker device provides an expandable end configured to reposition surrounding tissue. The surgical space maker device has a flexible member that includes: (i) a loop; and (ii) a strap. The surgical space maker device includes an elongated sheath having an end effector that is proximally attached to the flexible member. The surgical space maker device includes an elongate actuator received by the elongate sheath for longitudinal translation and distally connected to a distal end of the flexible member. Longitudinal movement in a first longitudinal direction of the elongate actuator deflects the distal end of the flexible member from a straight neutral state to a curved shape. In one or more embodiments, longitudinal movement in a second longitudinal direction opposite to the first longitudinal direction of the elongated member deflects the distal end of the flexible member from a straight neutral state to an inverted curved shape. The one of the curved shape and the inverted curved shape spaced apart from an unattached portion of the elongate actuator to define a three-dimensional working space.

These and other features are explained more fully in the embodiments illustrated below. It should be understood that, in general, the features of one embodiment also may be used in combination with features of another embodiment and that the embodiments are not intended to limit the scope of the invention.

BRIEF DESCRIPTION OF THE FIGURES

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating the teachings of the present disclosure are shown and described with respect to the figures presented herein.

DETAILED DESCRIPTION

Example embodiments according to the present disclosure are described and illustrated below to encompass devices, methods, and techniques relating to surgical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, among other things, surgical instruments and devices for creating surgical working spaces and related methods, and, more specifically, expandable space-making devices and related methods. Some example embodiments, according to at least some aspects of the present disclosure, may be useful in connection with ablation of cardiac tissue, such as to treat cardiac arrhythmias like atrial fibrillation. Some example embodiments, according to at least some aspects of the present disclosure, may at least partially shield an anatomical structure, such as to reduce the risk of thermal injury to non-targeted anatomical structures during an ablation procedure. The following description begins with an overview of an example embodiment, followed by the detailed description of various specific aspects of some example embodiments, and concludes with a description of example methods of using some example embodiments.

Generally, some example space-making devices, according to at least some aspects of the present disclosure, may include one or more expandable structures that can be delivered to surgical sites in a collapsed configuration (e.g., relatively small cross-section). When expanded, the surgical space maker devices may create working spaces in which other surgical instruments (e.g., endoscopes, ablation tools, etc.) may be used on target tissues.

Figure 1A:
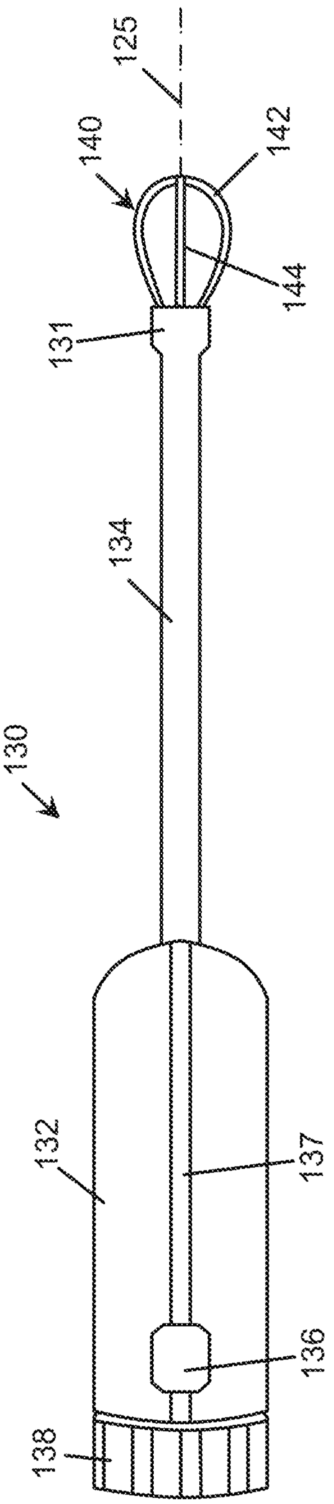
FIGS. 1A and 1B are illustrations of variations of surgical space-maker devices taken from a top view to better show a handle with a first actuator and a second actuator.
Figure 1B:
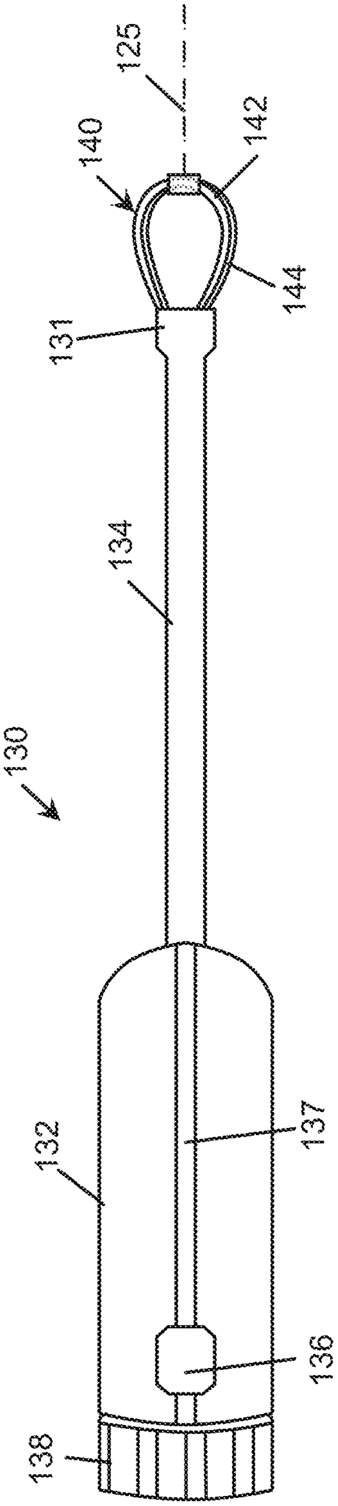

FIGS. 1A and 1B are illustrations of variations of surgical space-maker devices 130 taken from a top view to better show a handle 132 and a first actuator 136, and a second actuator 138. In this variation, the first actuator 136 is slidable within a channel 137, and the second actuator 138 is rotatable relative to the handle 132. The handle 132 includes a shaft 134 extending from the handle 132 where a distal end 131 (also referred to as a working end) of the shaft 134 houses a space-making frame 140. In the illustrated variations, the space-making frame 140 is advanced from the distal end 131 of the shaft 134 for purposes of illustration. In practice, the space-making frame 140 can be withdrawn into or adjacent to the distal end 131 of the shaft 134 during insertion and positioning of the device 130 at the start of a procedure. Variations of the space-making devices described herein can include rigid shafts. In alternate variations, the space-making device 130 can include any combination of rigid, malleable, steerable, arcuate shafts (e.g., curved), angled shafts (e.g., having a bend) or flexible shafts coupled to the handle 132. In addition, the illustrated shafts 134 are shown to have an increased diameter at the distal end 131. However, additional variations of the devices can include shafts with uniform diameters.

As discussed in more detail below, the actuators 136 138 are operably coupled to space-making frame 140 located at the distal end 131 of the shaft 134. In the illustration shown in FIG. 1A and FIG. 1B, the space-making frame 140 comprises a first frame member 142 and a second frame member 144. Typically, one or both of the frame members 142 144 comprises an arcuate shape. For purposes of explanation, the first frame member 142 is referred to as a first arcuate frame member 142, as shown in FIG. 1A. FIG. 1B illustrates both the first frame member 144 and the second frame member 144 as having arcuate shapes such that the second frame member would be referred to as a second arcuate frame member 144. Again, either or both frame members 142 144 can comprise arcuate shapes. The first frame member 142 and the second frame member 144 will be coupled together, which permits expansion of the space-making frame 140 into various geometries. As shown, frame members 142 144 are coupled together at a distal region of the space-making frame 140 and in general alignment with an axis 125 of the shaft 134. However, the coupling of the frame members 142 144 can be offset from the axis 125.

In one variation of the device 130, the first actuator 136 comprises slide configuration that moves axially relative to the handle 132 and is coupled to the first frame member 142, as will be described below. In such a configuration, the axial movement of the first actuator 136 results in the axial movement of the first frame member 142. The second actuator 138 includes a knurled dial/knob that rotates about an axis 125 of the shaft 134 and relative to the handle 132. The second actuator 138 includes components that are coupled to the second frame member 144 such that rotation of the second actuator 138 produces axial movement of the second frame member 144. Again, the terms "first" and "second" are intended to assist in identification of the various components. In practice, the slidable actuator and rotatable actuator could be coupled to either of the frame members. Moreover, the actuators shown in the illustration are for exemplary purposes only. Variations of the device can include linear/slide actuators (e.g., 135) for both frame members 142 144 or rotatable actuators (e.g., 138) for both frame members 142, 144. Therefore, in some variations, an actuator is simply a structure that can be operated to produce or prevent axial movement of an associated frame member.

Figure 1C:
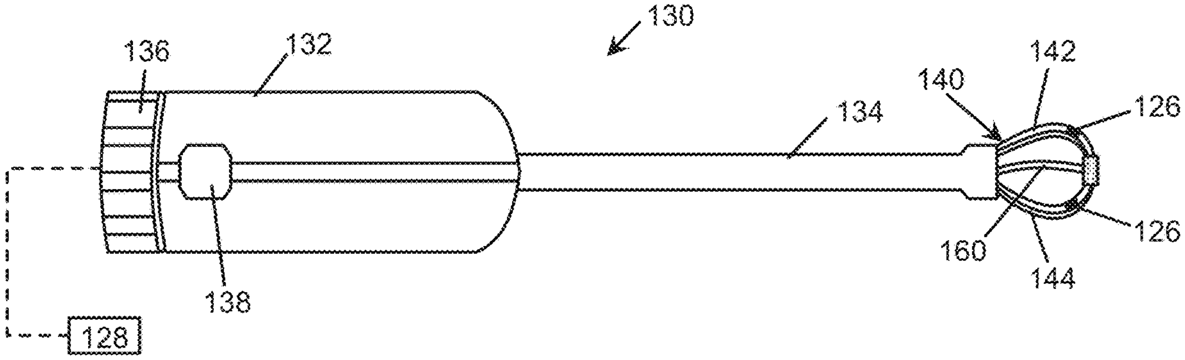
FIG. 1C illustrates another variation of a space-making device.

FIG. 1C shows additional optional features for use with any of the space-making devices described herein. It is contemplated that any aspects or features of any variation described herein can be combined with alternate variations of the device. For instance, as shown in FIG. 1C, the space-making frame 140 comprises a first frame member 142 having an arcuate configuration with an additional frame strut 160. Variations of the device 130 include a space-making frame 140 with at least one frame member having an arcuate configuration. However, the arcuate configuration of any frame member can include two or more struts 160.

FIG. 1C also illustrates an additional aspect of the devices 130 of the present disclosure where the space-making frame 140 includes one or more active elements 126. These active elements can be electrodes, sensors, or similar structures that apply therapy to or perform measurements of the tissue adjacent to the space-making frame 140. Such active elements can include but are not limited to, modalities such as ultrasound, RF energy, resistive heating elements, etc. In such cases, the device 130 will be configured to be coupled to a power supply or other appropriate device 128. In additional variations, a portion or an entirety of the space frame structure 140 can serve as an active element. In yet additional variations, portions of the space-making frame 140 can be coated where the active elements 126 are exposed areas of the space-making frame 140.

Figure 1D:
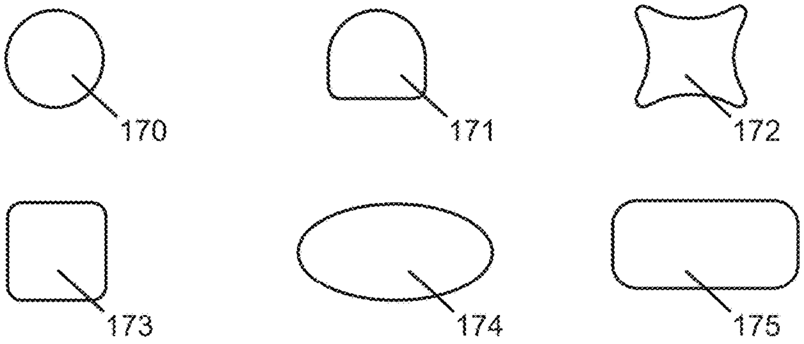
FIG. 1D illustrates variation shapes for struts forming the space-making frame.

FIG. 1D illustrates a non-exhaustive example of cross-sectional shapes of the struts that form the space-making assemblies 140 described herein. The cross-sectional shapes can include circular 170, non-symmetrical shapes 171, shapes with irregular surfaces 172, square 173, oval 175, rectangular 175, as well as any other shape. In addition, any frame member can include a strut with different cross-sectional shapes and/or two struts with different cross-sectional shapes.

Figure 2B:
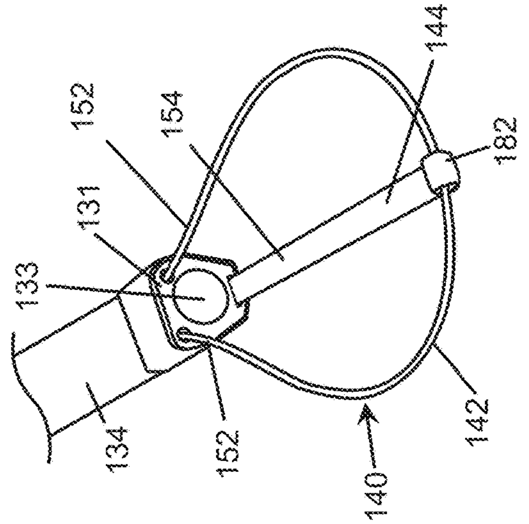
FIGS. 2A through 2C illustrate some variations of space-making frames extending from a distal end of a shaft.
Figure 2C:
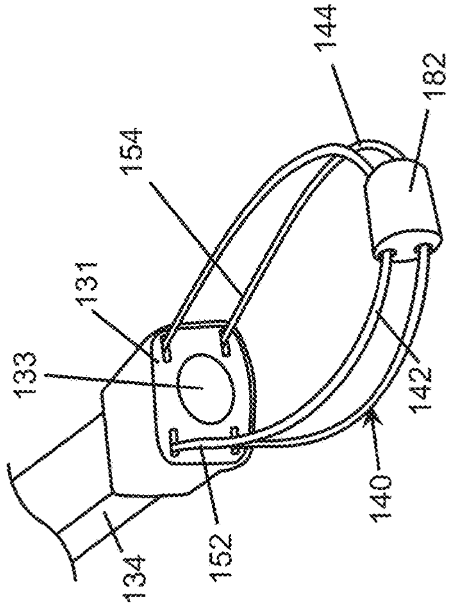
Figure 2A:
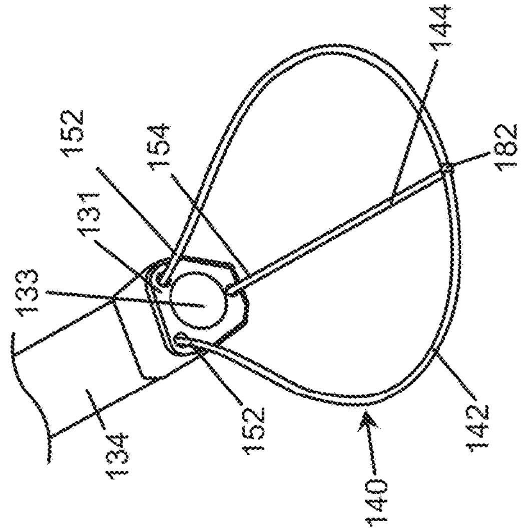

FIGS. 2A through 2C illustrate some variations of space-making frames 140 extending from a distal end 131 of a shaft 134. FIGS. The use of a wire-frame assembly provides advantages over a balloon or other inflatable space-making device since the wire-frame assembly increases the surface area of the tissue that can be contacted with a treatment or visualization device. Moreover, the space-making frame 140 can be selected such that it is compliant when working against moving surfaces such as the lungs or heart. This compliance minimizes the chance that the space-making frame 140 reduces the output of such organs by restricting their ability to move. The space-making frame 140 described herein can include frame members 142 144 having similar compliance characteristics, or the compliance of the frame members 142 144 can be different such that one is stiffer or less compliant than the other. In addition, any of the frame assemblies can be coated with various polymers or other substances to increase the lubricity of a part or all of the space-making frame 140. The coatings can provide therapeutic benefits as well by preventing clotting, increasing atraumatic effects, etc.

FIGS. 2A and 2B are similar to the variation shown in FIG. 1A, where the space-making frame 140 includes a first arcuate member 142 having two struts 152 spaced apart that extend proximally and are ultimately coupled to an actuator as discussed below. The space-making frame also includes a secondary frame member 144 that is not arcuate in shape but where a strut 154 also extends proximally for coupling to an actuator. It is contemplated that one or more of the struts 152 154 do not extend within the shaft 134 but along an exterior (either through a separate tube or separate passage.) Alternatively, the returning struts 152 154 can extend within the working channel 133 or within separate lumens in the event that the shaft 134 comprises a multi-lumen configuration. The strut 154 of FIG. 2A comprises a narrow configuration, while the strut of FIG. 2B comprises a wider configuration. Regardless, the secondary frame member 144 of FIGS. 2A and 2B are coupled to the first arcuate strut 142 at a connection point 182 at a distal region of the space-making frame 140 and in somewhat alignment with an axis of the shaft 134. FIG. 2C illustrates a different variation, similar to that shown in FIG. 1B, where the space-making frame 140 extends from the distal end 131 of a shaft 134 and comprises a first arcuate member 142 and a second arcuate member 144. Each of these comprises struts 152 154 that allow coupling of the respective arcuate member 142 144 with a respective actuator. The arcuate members 142 144 are coupled together at coupling location 182, which in this variation shows the location as being an atraumatic connector. Alternatively, the frame members 142 144 can be joined together. FIGS. 2A to 2C also show the space-making frames 140 located adjacent to an opening or working lumen 133 of the shaft 134. As described below, this permits advancement of any medical device or instrument through the shaft 134 and into a space created by the space-making frame when expanded. Typically, one or both of the frame members 142 144 are fabricated from an elastic or resilient material, including but not limited to Nitinol, steel, etc. The material should allow the space-making frame to assume a range of desired shapes and to return to an undeployed profile when desired.

Figure 3A:
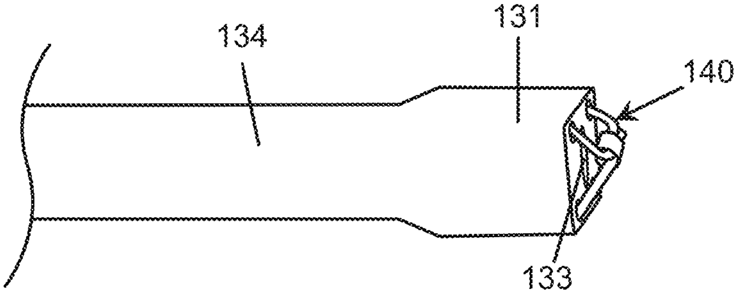
FIGS. 3A to 3D illustrate a space-making frame being advanced from an undeployed configuration to multiple expanded configurations.
Figure 3B:
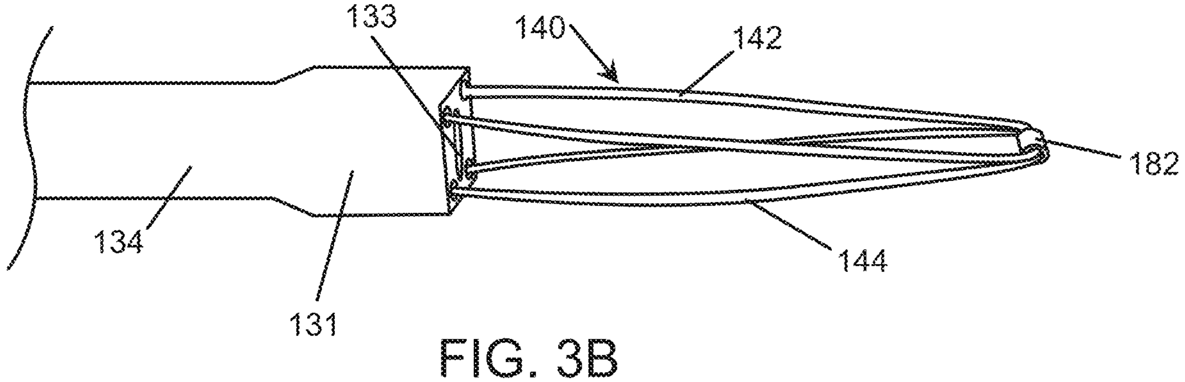

FIGS. 3A to 3D illustrate a space-making frame 140 being advanced from an undeployed configuration to multiple expanded configurations. FIG. 3A illustrates an optional state of the device where the space-making frame 140 is withdrawn either entirely or significantly within the distal end 131 of the shaft. FIG. 3B illustrates a neutral position where the space-making frame 140 is advanced in a distal direction. It is noted that devices under the present disclosure can have an undeployed configuration that starts in the neutral position, as shown in FIG. 3B. Regardless, when the first arcuate member 142 and second arcuate member 144 are both axially moved in the same direction using their respective actuators (not shown in FIG. 3B), the space-making frame 140 translates in an axial direction relative to an axis of the shaft 134.

Figure 3C:
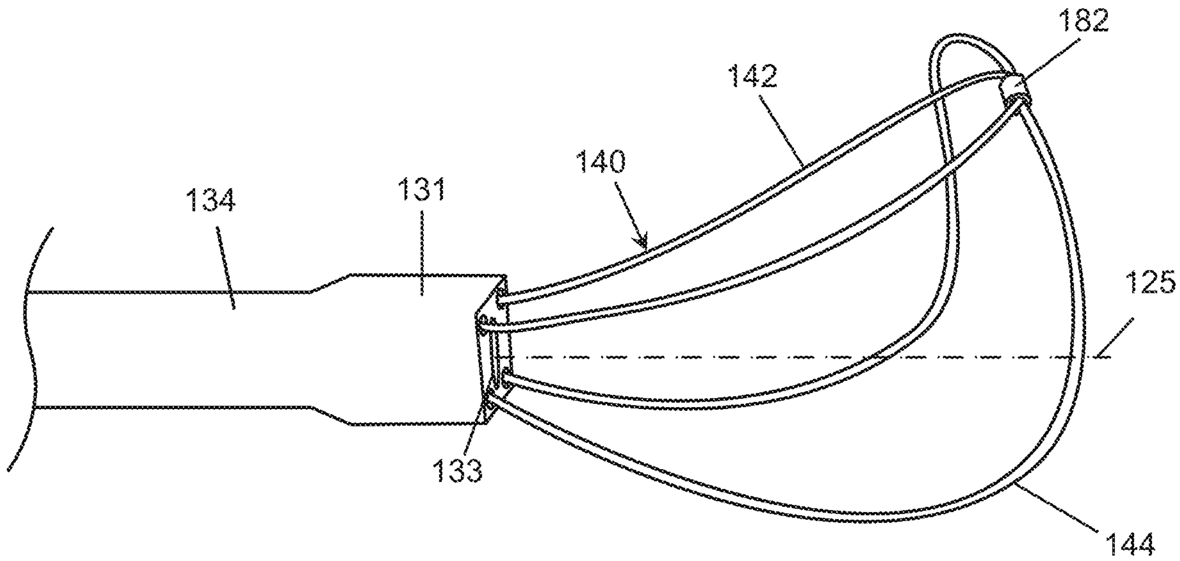

FIG. 3C shows a state of the device where the first frame member 142 is withdrawn or prevented from moving distally. As noted below, the respective actuator coupled to the first frame member can prevent movement of the first frame member 142 or can be held stationary. The actuator coupled to the second frame member 144 is operated to advance the second frame member 144 distally. Since the second frame member 144 is restrained by the first frame member 142 at the coupling region 182, the space-making frame 140 assumes a shape where the first frame member 142 forms an upward arc with the second frame member 144 expanding the space-making frame 140 in both height and width (and optionally length) as compared to the neutral position of FIG. 3B. original intended working position. The actuator coupled to the first frame member 142 can be operated to push the first frame member 142 in a distal direction as needed to increase a profile of the frame members and overall arc size of the space-making frame 140. As will be discussed below, the expanded space-making frame 140 separates adjacent anatomic structures to allow for one or more tools to advance from the working lumen 133 into the space created by the space-making frame 140.

Figure 3D:
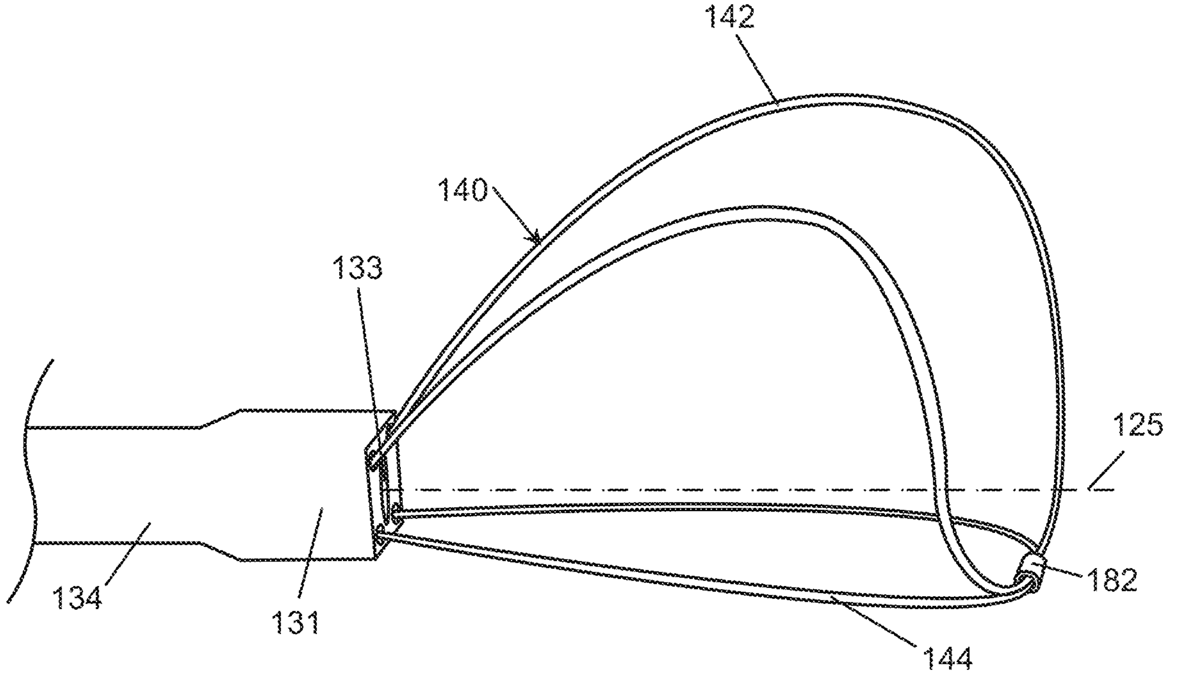

FIG. 3D illustrates the space-making frame 140 of FIG. 3C when the actuator coupled to the first frame member 142 advances the first frame member axially from the working end 142 while the actuator coupled to the second frame member 144 axially withdraws the second frame member 144 causing the formation of an inverted arc by the first frame member 142. As noted above, operation of the actuators on the device allows for altering the shape of the expanded space-making frame 140 as desired for the local anatomy or desired procedure. The construction of the space-making frame 140, namely with at least two independent actuators that can axially adjust two respective frame members, in conjunction with at least one frame member having an arcuate shape, allows a user to symmetrically or asymmetrically expand the space-making frame 140 relative to an axis 125 of the shaft 134 or working channel 133. For instance, in FIG. 3C, the space-making frame 140 expands asymmetrically relative to the axis 125. In FIG. 3D, either or both of the frame members 142 144 can be adjusted such that the space-making frame 140 is expanded to one side of the axis 125. The custom adjustment of the space-making frame 140 can also occur without repositioning and/or rotation of the shaft 134. However, the ability to reposition and rotate the shaft, as well as the ability to re-shape the space-making frame 140, provides a user with the ability to controllably create a space within anatomy.

Figure 4A:
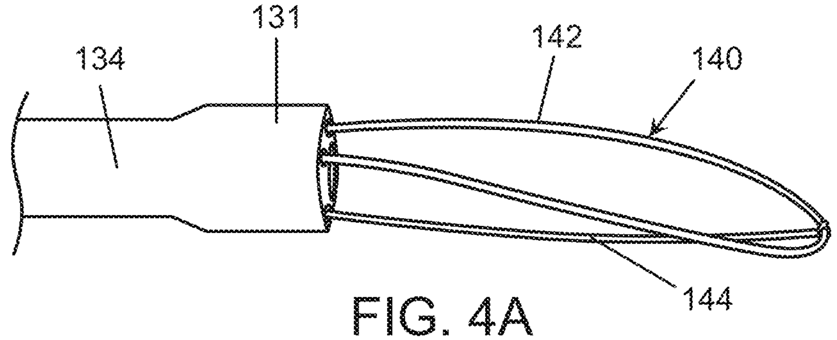
FIGS. 4A to 4C illustrate a space-making frame being advanced from an undeployed configuration to multiple expanded configurations where the space-making frame comprises a first arcuate member and a secondary frame member that is linear and not arcuate.
Figure 4B:
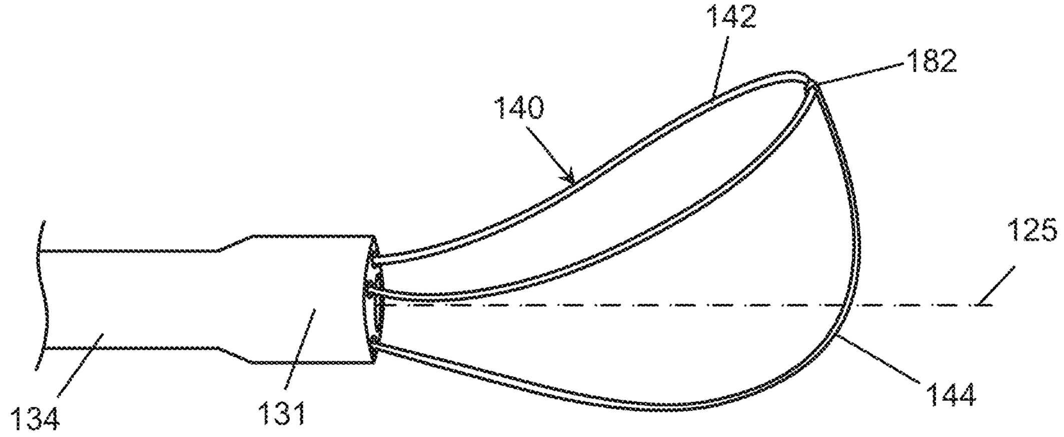
Figure 4C:
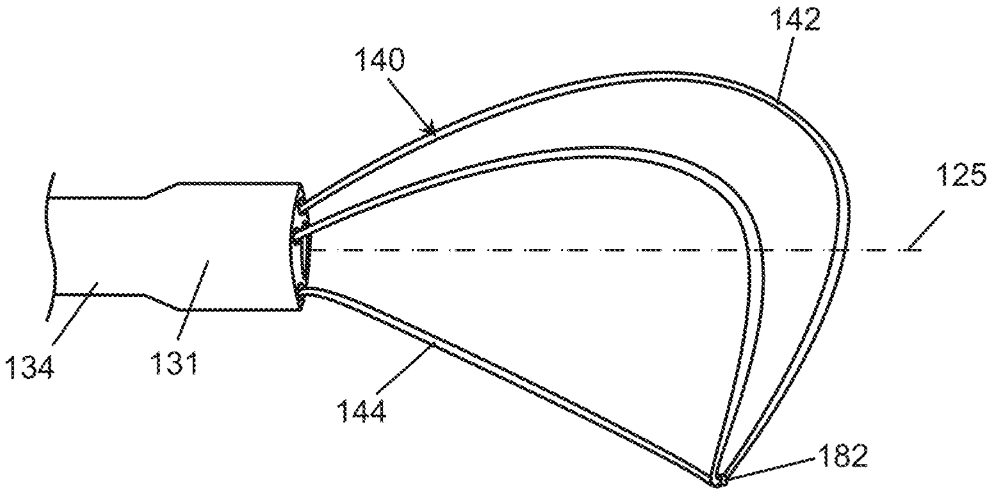

FIGS. 4A to 4C illustrate a space-making frame 140 being advanced from an undeployed configuration to multiple expanded configurations where the space-making frame 140 comprises a first arcuate member and a secondary frame member 144 that is linear and not arcuate. FIG. 4A illustrates a neutral state of the space-making frame 140 where the space-making frame 140 is distal to a working end 131 of the shaft 134.

FIG. 4B illustrates the space-making frame 140 of FIG. 4B when the actuator that is coupled to the first frame member 142 remains stationary or is withdrawn towards the shaft 134 while the second frame member 144 advances distally from the working end 131. Again, because the frame members 142 144 are coupled together at region 182, the second frame member 144 forms an arc, as shown in FIG. 4B to expand the space-making frame 140 in one or more dimensions (e.g., width, height, length).

FIG. 4C shows a state of the space-making frame 140 when the second frame member 144 is withdrawn or remains stationary, and the first frame member 142 is advanced. This causes the formation of an inverted arc, as shown by FIG. 4C. As with the variations shown above, the frame members 142 144 can be manipulated using the actuators to adjust a size of the space within the boundary of the space-making frame 140.

FIGS. 4B and 4C also show the benefit provided by the construction of the space-making frame 140, namely that at least two independent actuators allowing for axial adjustment of two respective frame members, in conjunction with at least one frame member having an arcuate shape, allows a user to asymmetrically expand the space-making frame 140 relative to an axis 125 of the shaft 134 or working channel 133. For instance, in FIG. 4B, the space-making frame 140 expands asymmetrically relative to the axis 125.

FIG.e in FIG. 4C, either or both of the frame members 142 144 can be adjusted such that the space-making frame 140 moves from the shape shown in FIG. 4B to the shape shown in 4C without repositioning and/or rotation of the shaft 134.

Figure 5A:
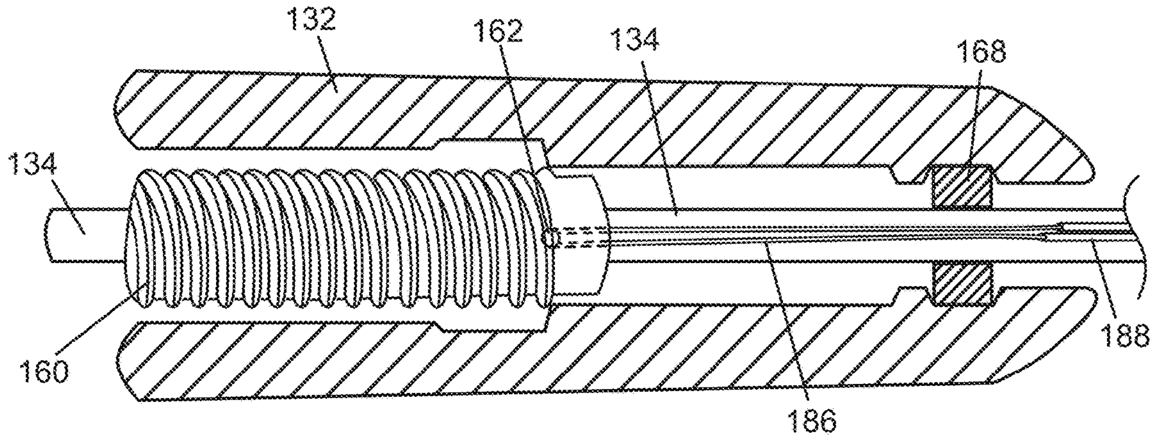
FIGS. 5A to 5C show a partial cross-sectional view of a handle, similar to that shown in FIG. 1A FIG. 6A also illustrates one example of a method of use of a space-making device 130 positioned over a posterior surface of a heart.
Figure 5B:
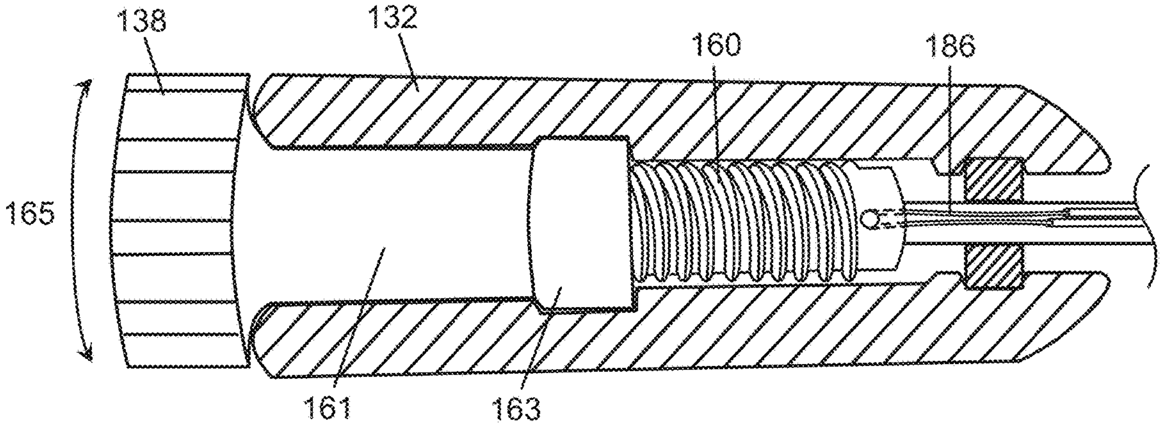
Figure 5C:
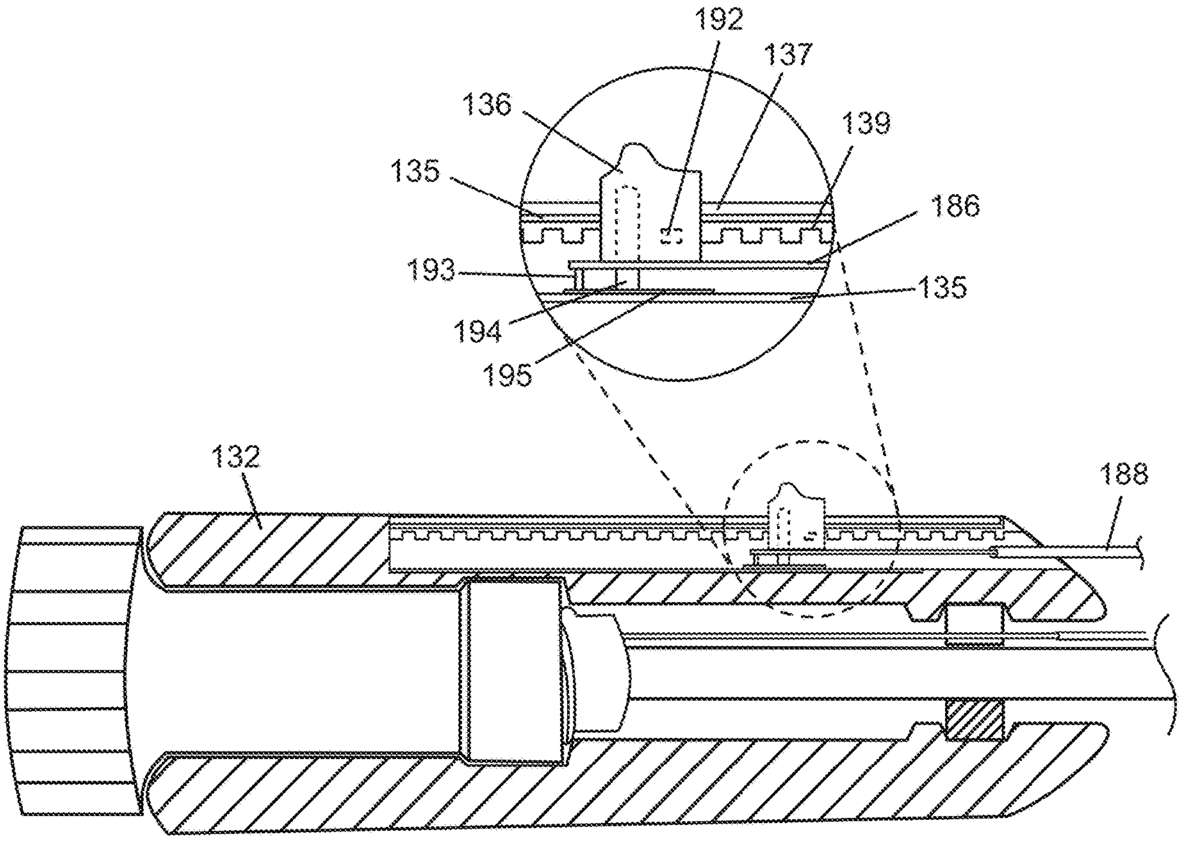

FIGS. 5A to 5C show a partial cross-sectional view of a handle 132, similar to that shown in FIG. 1A, to illustrate examples of actuators that are coupled to the space-making frame (not shown in FIGS. 5A to 5C). The devices described herein are not limited to the actuator and actuator assemblies shown. Instead, any actuator known in the associated mechanical and medical device art can be used in place of the exemplary actuators discussed below.

FIG. 5A shows a cross-sectional top view of a handle 132 to reveal an actuator component comprising a threaded driver 160 that houses linkages 186 that are coupled to one of the frame members. In this illustration, an actuator body 161 is omitted for purposes of showing a mechanism of rotational movement of the actuator handle to produce linear movement of a threaded driver 160 to move the linkages 186. Alternatively, in place of linkages 186, struts from the respective frame member can be directly coupled to the threaded driver 160. The linkages 186 (or struts) are affixed to the threaded driver 160 using any mechanical (e.g., a set screw) or chemical fixation (e.g., adhesive). As shown, a shaft 134 extends through the handle 132 and threaded driver 160 to permit any medical device or instrument to be advanced through a lumen of the shaft from the proximal end of the space-making device to the working end. The shaft is positioned in the handle 132 either by use of a structure 168 (e.g., a disk) or by the body of the handle 132 itself. FIG. 5A also shows linkages 186 (or struts) that are exterior to the shaft 134 and can optionally pass through tubing 188 that provides a path to the space-making frame.

FIG. 5B shows a partial cross-sectional view of the handle 132 to illustrate the actuator 138 with a knob structure at the proximal end of the handle 132 and an actuator body 161 extending within the handle 132 of the device over the threaded driver. The actuator body can include one or more threads in any portion of the actuator body 161. These threads mate and engage threads in the threaded driver 160. This allows the actuator body 161 to function as a nut when coupled to the threaded driver 160 such that rotation 165 of the actuator 138 causes axial movement of the threaded driver 160 and axial movement of one or more linkages 186 (or struts if directly coupled to the frame member. The actuator body 161 can have one or more retaining features 163 to retain the actuator within the handle 132.

FIG. 5C illustrates a cross-sectional side view of the handle 132 (where the handle is rotated 90 degrees from the view of FIG. 5A) to reveal another variation of an actuator 136 having linkages 186 (or struts) that are coupled to a respective frame member of the space-making frame. Again, the linkages 186 (or struts) can pass outside of the shaft 134 through one or more tubing 188 that provide a path to the space-making frame. In this variation, the actuator 136 slides along an axis of the handle 132 within a channel 137 along any number of sliding surfaces 135 to move the respective frame member. FIG. 5C also shows the actuator 136 as using one or more linkages 186 as spring members to assist in locking the actuator 136 with respect to the handle 132. As noted above, the linkages 186 can comprise the struts of the space-making frame instead of a separate component. For this variation, the linkage or linkages 186 are resilient (e.g., Nitinol or other resilient material) such that they bias a locking structure 192 of the actuator 136 against a locking surface 139 to prevent movement of the actuator 136. As shown, the linkage or linkages 186 are offset from a sliding tab 195 via mechanical fixation 193. This biases the actuator 136, which can be slidable over a post 194, in an upward direction, causing the locking structure 192 to engage the locking surface 139. To operate the actuator 136, a user must press downwards on the actuator 136 to deflect the linkage 186 and disengage the locking element 192 from the locking surface 139. Then, the user can slide the actuator 136 within the channel 137 over any number of sliding surfaces 135. This causes axial movement of the linkage 186 and associated frame member. It is noted that the length of the channel 137 and locking surface 139 shown in FIG. 5C is for illustrative purposes only. These features can extend over a greater or shorter length of the handle 132. Moreover, any number of locking configurations known can be employed (e.g., using a separate spring member, a rachet configuration, etc.)

Figure 6A:
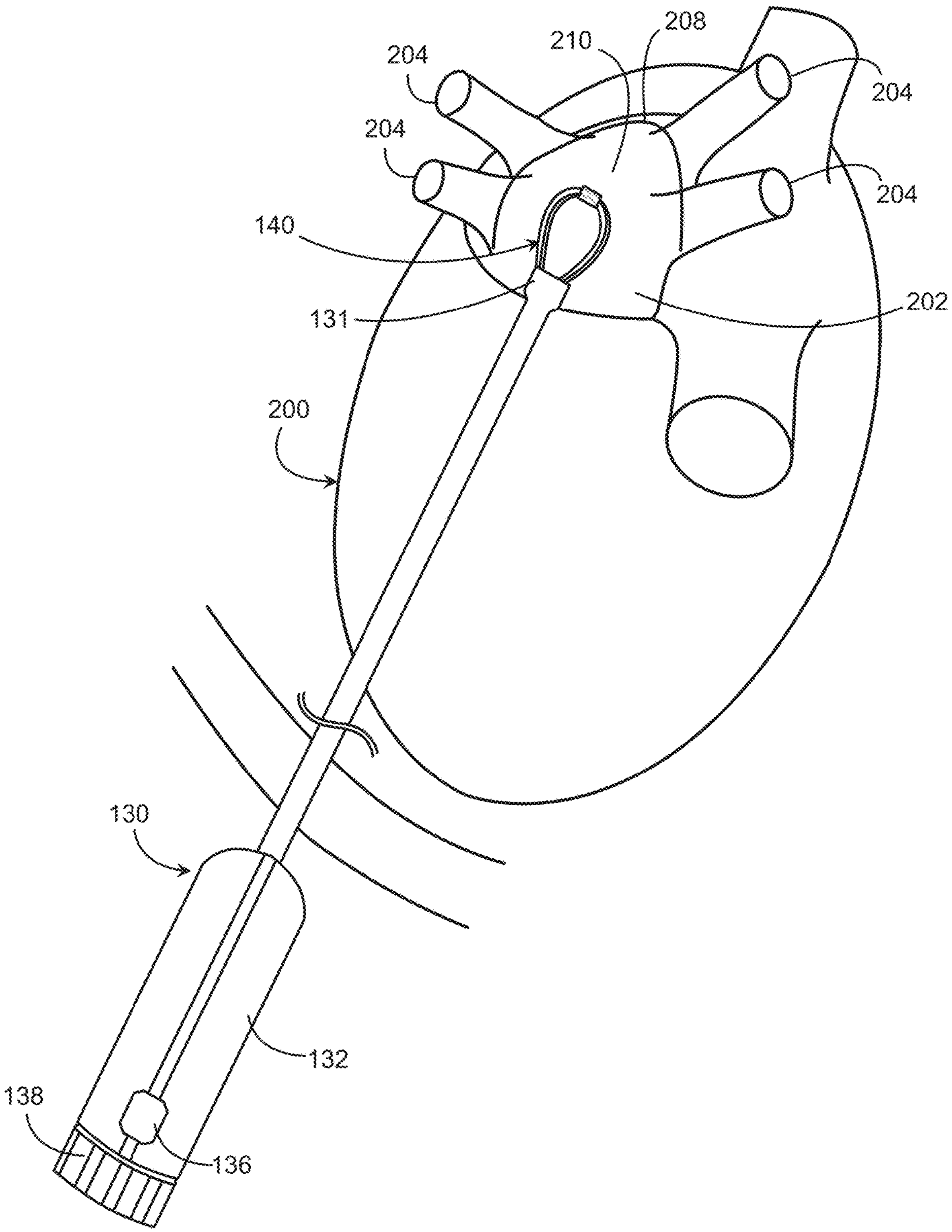
FIG. 6B illustrates expansion of the space-making frame 140 to create a temporary space adjacent to the tissue.

FIG. 6A shows a posterior left atrium 202 of the heart 200, which may be a target for the therapeutic treatment of atrial fibrillation. The left atrium 202 is located generally on the posterior (rear) surface of the heart 200 and receives blood from the lungs through the pulmonary veins 204. The pericardial sac 206, the sac containing the heart 200, is attached to the surface of the heart 201 at pericardial reflections 208 near the pulmonary veins 204. These pericardial reflections 208, in connection with the pulmonary veins 204, define a potential space on the posterior side of the left atrium 202 referred to as the oblique sinus 210. Some surgical procedures, such as ablation of portions of the left atrium 202, may involve operations performed within the oblique sinus 210.

FIG. 6A also illustrates one example of a method of use of a space-making device 130 positioned over a posterior surface of a heart 200. The working end 131 of the device 130 is positioned adjacent to a region of interest, in this example the region of interest is the oblique sinus 210 near the pulmonary veins 204. As shown, the device 130 is generally positioned when the space-making frame 140 is in a neutral or delivery position while the handle 132 remains outside of the anatomy to allow a user to access the actuators 136, 138. In addition, the space-maker device 130 can be used with or without a delivery sheath and can be guided using any type of imaging (e.g., endoscopy, fluoroscopy, virtual, etc.).

Figure 6B:
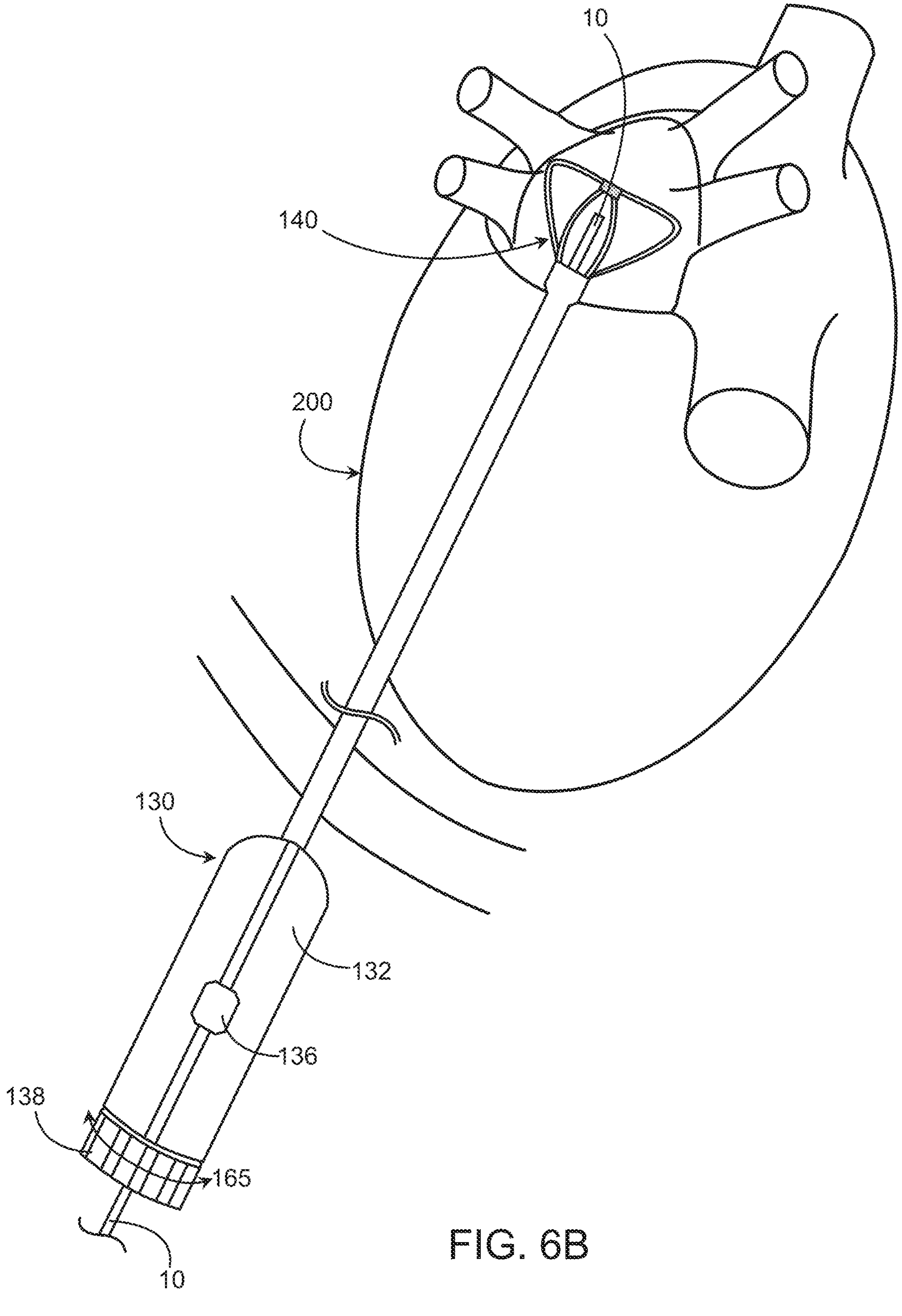

FIG. 6B illustrates the expansion of the space-making frame 140 to create a temporary space adjacent to the tissue. As noted above, the ability to independently control the space-making frame 140 using at least two actuators 136 138 allows the operator the ability to select the desired orientation and shape of the space-making frame 140. As noted above, the use of a wire-based space-making frame 140 is especially beneficial when attempting to create a cavity or space adjacent to contoured surface. The compliancy of the space-making frame 140 described herein allows the frame 140 to follow the natural contour of the anatomy as opposed to a pressurized (e.g., a balloon) or another rigid structure. In the case of cardiac applications, the wire space-making frame 140 flexes when it moves cardiac tissue to permit the beating of the heart and minimize compromising any cardiac output. Also, the wire space-making frame 140 increases the target area to permit instruments 10 to move within the space. Such instruments can include treatment devices, visualization devices, access devices, etc. Although not shown, as described in FIG. 1C, the device used to create a space can include any number of active elements on the space-making frame 140 (as well as or alternatively the shaft). The method can further include applying energy from one or more active elements to produce a therapeutic effect (e.g., ablate tissue, coagulate tissue, deliver a therapeutic substance, etc.) or to map or pace electrical currents within the tissue.

Figure 7A:
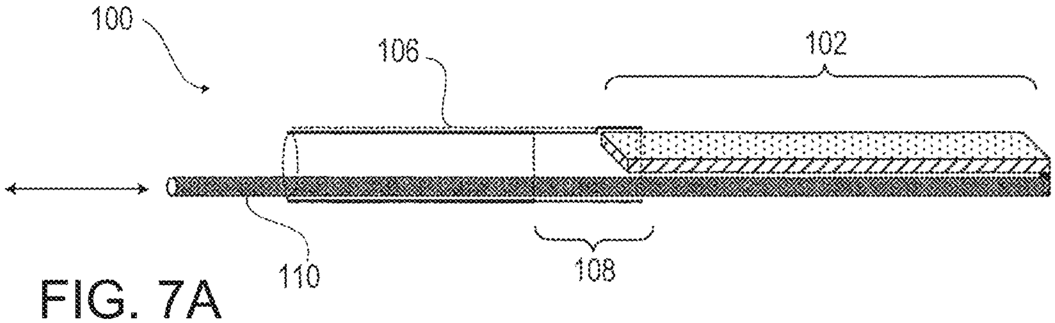
FIGS. 7A to 7D illustrate another variation of a space-making device.

FIG. 7A is a diagram of an another example of a surgical space maker device 100 in a neutral, unexpanded state. The surgical space maker device 100 has s a distal expanding portion 102 including or essentially comprising flexible member 104. The flexible member 104 may be one of (i) a loop; and (ii) a strap. The surgical space maker device 100 includes an elongate sheath 106 having an end effector 108 that is proximally attached to the flexible member 104. The surgical space maker device 100 includes an elongate actuator 110 received by the elongate sheath 106 for longitudinal translation and distally connected to a distal end of the flexible member 104. In a neutral position of the elongate actuator, the flexible member 104 is in a straight neutral state in proximity to the elongate actuator 110.

Figure 7B:
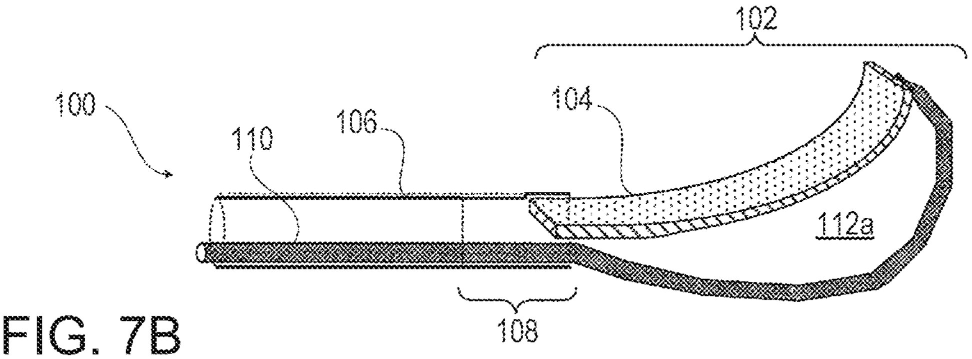

FIG. 7B is a diagram of the example surgical space maker device 100 with the distal expanding portion 102 in an expanded state. Longitudinal translation or movement in a first longitudinal direction (e.g., proximal to distal) of the elongate actuator 110 deflects the distal end of the flexible member 104 from a straight neutral state (FIG. 7A) in proximity to the elongate actuator 110 to a curved shape spaced apart from an unattached portion of the elongate actuator 110 to define a three-dimensional working space 112*a*.

Figure 7C:
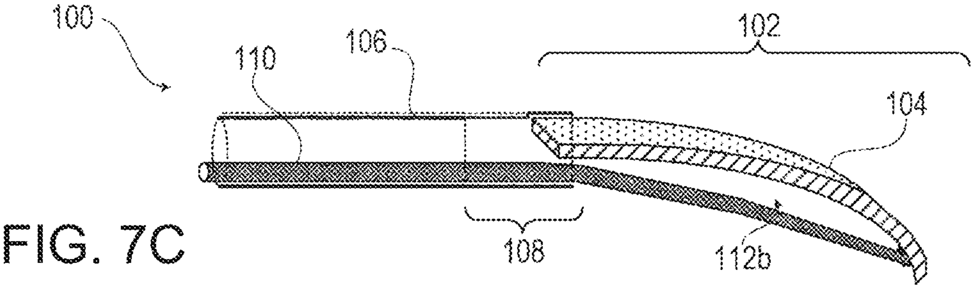

FIG. 7C is a diagram of an example of a surgical space maker device 100 with the distal expanding portion 102 in an inverted expanded state. Longitudinal translation or movement in a second longitudinal direction (e.g., distal to proximal) opposite to the first longitudinal direction of the elongate member 110 deflects the distal end of the flexible member 104 from a straight neutral state (FIG. 7A) in proximity to the elongate actuator 110 to an inverted curved shape spaced apart from an unattached portion of the elongate actuator 110 to define a three-dimensional working space 112*b*.

Figure 7D:
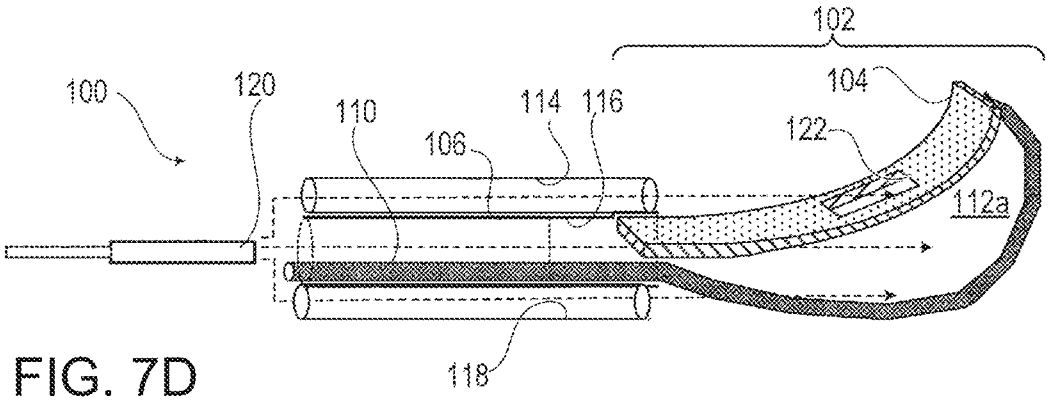

FIG. 7D is a diagram of the example surgical space maker device 100 with the distal expanding portion 102 in an expanded state to create the three-dimensional working space 112*a* for an insertable instrument 120 as scopes, ablation probes, etc. In one or more embodiments, the sheath 106 includes one or more of an upper external lumen 118, an internal lumen 116, and a lower external lumen 118 having a respective distal opening aligned with one of an interior or an exterior of the three-dimensional working spaces 112*a*-112*b* for insertion of the insertable instrument 120. Flexible member 104 may include one or more openings 122.

In one or more embodiments, the flexible member 104 of the surgical space maker device 100 is a wire loop, and the elongate actuator 110 is a wire. In one or more embodiments, the flexible member 104 of the surgical space maker device 100 is a first wire loop, and the elongate actuator 110 is a second wire loop. In one or more embodiments, the flexible member 104 of the surgical space maker device 100 is a first portion of a strap, and the elongate actuator 110 is the second portion of the strap distally connected to the first portion of the strap at a folded crease. In one or more particular embodiments, the strap has the opening 122.

Example methods of creating a working space using example space-making devices according to at least some aspects of the present disclosure are described below. The following description focuses on use of the example surgical space maker device 100 described above; however, at least some of the operations may also be applicable to other space-making devices according to at least some aspects of the present disclosure. Further, the example methods described below focus on the use of example space-making devices in the context of ablation of portions of the left atrium, such as in connection with treatment of atrial fibrillation; however, example methods according to at least some aspects of the present disclosure may be utilized in connection with surgical procedures performed at other anatomical locations and/or for other purposes.

Figure 8A:
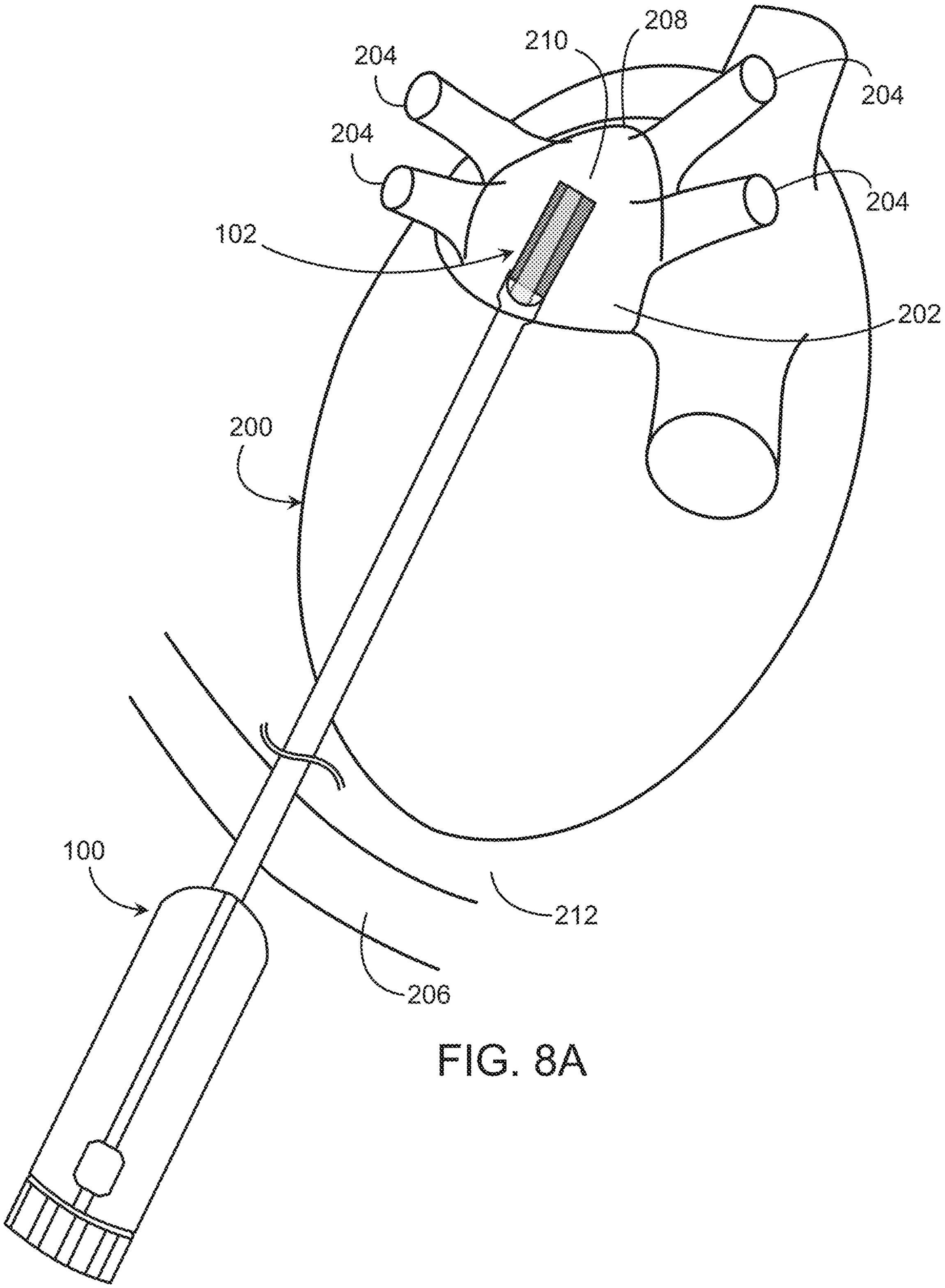
FIG. 8A is a simplified posterior perspective view of a heart illustrating an example method of using an example surgical space maker device in an unexpanded state, according to one or more embodiments.

FIG. 8A is a simplified posterior perspective view of a heart 200 illustrating an example method of using an example surgical space maker device 100 with a distal expanding portion 102 in an unexpanded state. FIG. 2B is a simplified posterior perspective view of the heart 200 illustrating an example method of using an example surgical space maker device 100 with a distal expanding portion 102 in an expanded state, with particular reference to FIG. 8A, a posterior left atrium 202 of the heart 200 may be an anatomic ablation target for the treatment of atrial fibrillation.

Some example methods of creating a surgical working space may include directing a surgical space-making device 100 to a surgical site (e.g., the oblique sinus 210), which may be proximate a target tissue (e.g., a left atrium). For example, a surgeon may obtain access into the pericardial space 212 (e.g., the interior of the pericardium 206). This may be accomplished using surgical and/or percutaneous methods through the skin and intervening anatomical structures, such as via a sub-xiphoid and/or intercostal approach. The surgical space-making device 100 (e.g., the sheath 106) can be advanced into the pericardial space 212, such as into the oblique sinus 210. In other example embodiments, a delivery sheath separate from the surgical space-making device 100 may be advanced into the pericardial space 212 (e.g., oblique sinus 210), and the surgical space-making device 100 may be delivered via the separate delivery sheath. The surgical space maker device 100 and/or delivery sheath may be guided using endoscopy and/or fluoroscopy, for example.

Figure 8B:
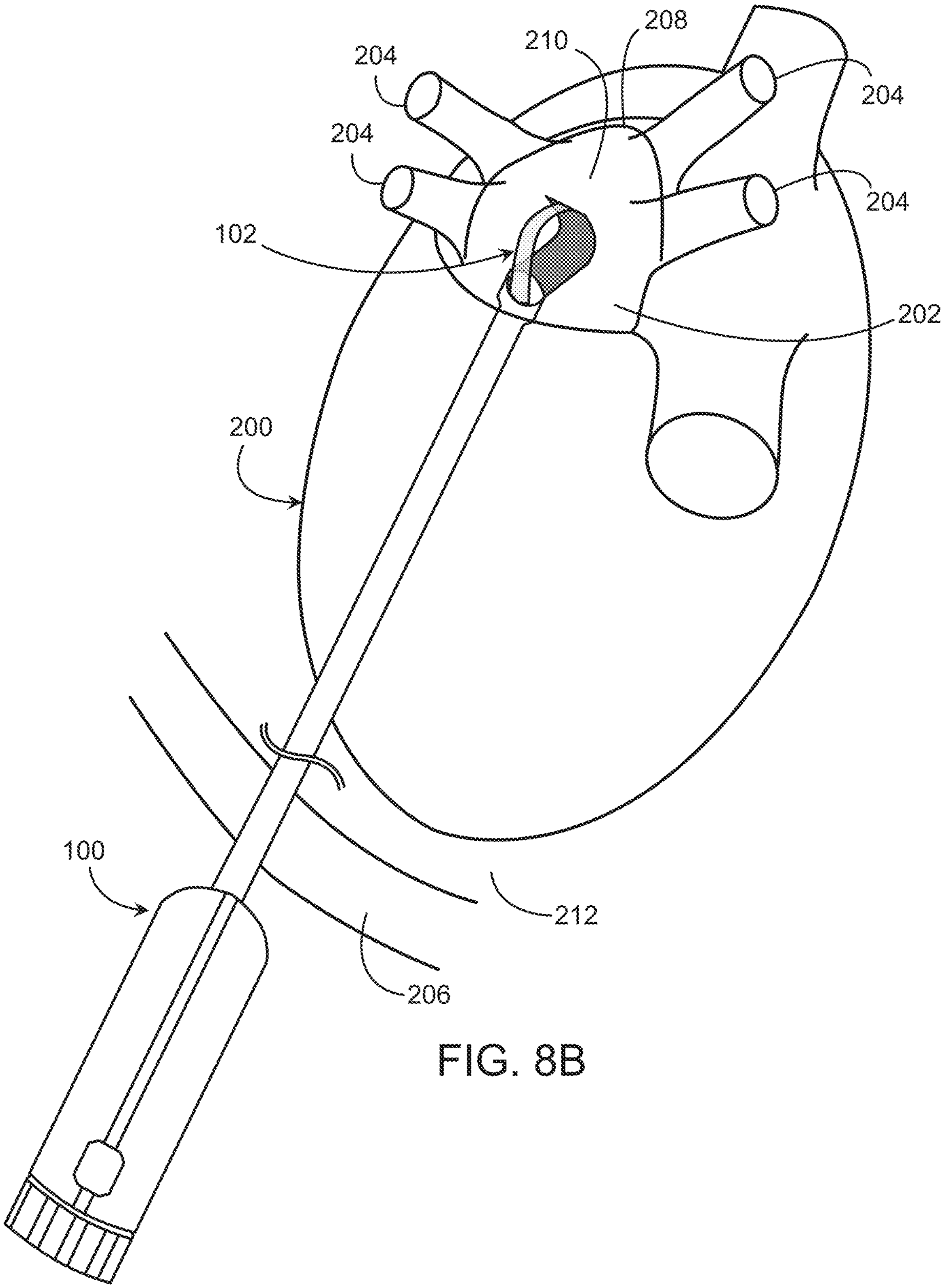
FIG. 8B is a simplified posterior perspective view of a heart illustrating an example method of using an example surgical space maker device in an expanded state, according to one or more embodiments.

With reference to FIG. 8B, the distal expanding portion 102 of the surgical space maker device 100 may be deployed, such as into the oblique sinus 210. In some example embodiments, the distal expanding portion 102 may be at least partially contained within the sheath 106 while the sheath 106 is advanced into the pericardial space 212 through the pericardium 206. Then, the s distal expanding portion 102 may be unsheathed from the sheath 106 to deploy the distal expanding portion 102 into the oblique sinus 210. In other example, embodiments, the surgical space maker device 100 may be inserted through a separate delivery sheath, and the distal expanding portion 102 may be extended distally beyond the distal end of the separate delivery sheath and into the oblique sinus 210. Proximal components of the surgical space maker device 100, such as a proximal portion of the sheath 106 and/or proximal portions of the elongate actuator 110, may remain outside of the skin.

After the distal expanding portion 102 is at least partially expanded, one or more surgical instruments 120 may be delivered into the three-dimensional working space. For example, one or more visualization instruments (e.g., endoscopes) and/or one or more ablation instruments (e.g., radiofrequency ablation instruments) may be positioned and/or utilized in and/or near the working space. Generally, the entry from the skin incision into the pericardial space 212 may cross multiple tissue planes, and/or the path from the incision to the oblique sinus 210 may be three-dimensional. The surgical space-making device 100 may provide a track that other surgical instruments may follow to the oblique sinus 210. In some examples, embodiments, one or more surgical instruments 120 can be delivered to the working space via the sheath 106 of the surgical space maker device 100. In some example embodiments, one or more surgical instruments 120 (FIG. 7D) may be delivered to the working space separately from the surgical space maker device 100, such as adjacent to the surgical space maker device via the same access path and/or via another access path.

In some example embodiments, the surgical instruments 120 (FIG. 7D) may be used to visualize anatomical landmarks, guide ablation tools, ablate target tissues, etc., as required to accomplish the purpose of the surgical procedure. For example, an endoscope may be utilized to visualize anatomical variations of the oblique sinus boundaries, which may vary substantially from patient to patient. Creation of the working space 112*a* and/or facilitating visualization of the anatomical landmarks may assist in standardizing some aspects of surgical procedures, such as ablation lesion placement, regardless of patient anatomical variations and user (e.g., surgeon) technique.

In some example embodiments, at least a portion of the distal expanding portion 102 may act as a shield to reduce the risk of injury to tissues near the surgical site. Alternatively, or in addition, the distal expanding portion 102 may be enclosed within a bag. In an example, the end effector 108 and loops of a wire-based variation may be covered in a plastic covering or bag providing a surgical space maker device 100 that is more atraumatic, better shielding to the esophagus, and may facilitate use of some ablation tools. For example, the esophagus lies immediately posterior to the oblique sinus 210 and may be injured when ablation is performed in the oblique sinus 210. In some example embodiments, the distal expanding portion 102 may protect the esophagus from injury when thermal ablation is performed on the left atrium 202. After the operations at the surgical site within the working space 112*a* are complete, the surgical instruments 120 (FIG. 7D) may be withdrawn.

After the distal expanding portion 102 of the surgical space maker device 100 has been returned to the unexpanded state, the surgical space maker device 100 may be withdrawn from the oblique sinus 210. In some example embodiments, the distal expanding portion 102 may be withdrawn at least partially within the sheath 106, and then the sheath 106 may be withdrawn from the oblique sinus 210. The surgical space-making device 100 may be withdrawn from the patient's body (e.g., via the pericardium 206 and/or the skin). Example methods of manufacturing space-making devices and components thereof may include operations associated with acquiring, producing, and assembling various parts, elements, components, and systems described herein.

Although some example embodiments have been described above in connection with realizing a working space from a potential space, some example embodiments may be used to dilate (e.g., make wider or larger) anatomical openings and/or to develop tissue planes, such as by separating adjacent, at least partially connected tissue layers.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

We claim:

1. A surgical space-making device for separating anatomic structure to permit use of a medical device at a region of interest, the surgical space-making device comprising:

a handle having a first actuator and a second actuator each independently operational;

a shaft extending distally along an axis from the handle, the shaft having an interior lumen;

a working end at a distal end of the shaft where the interior lumen is open at the working end;

a space-making frame located at the working end, the space-making frame comprising an arcuate frame member moveable by operation of the first actuator and a secondary frame member moveable by operation of the second actuator, where the arcuate frame member and secondary frame member are coupled together, wherein at least the first actuator is spring-biased to a locking position by a portion of the arcuate frame member;

wherein operation of the first actuator and operation of the second actuator to move the arcuate frame member and the secondary frame member in a same direction causes the space-making frame to move axially relative to the working end; and wherein operation of the first actuator and operation of the second actuator to move the arcuate frame member and the secondary frame member relative to each other causes the space-making frame to expand away from the axis to an expanded profile permitting separation of anatomic structures adjacent to the working end to create a space adjacent to the region of interest such that the medical device can be advanced through the interior lumen towards the region of interest.

2. The surgical space-making device of claim 1, wherein the space-making frame is compliant and configured such that an anatomical movement of an organ causes the space-making frame to deflect.

3. The surgical space-making device of claim 1, wherein the secondary frame member comprises a secondary arcuate frame member.

4. The surgical space-making device of claim 1, wherein the secondary frame member comprises a single strut.

5. The surgical space-making device of claim 1, wherein at least the arcuate frame member comprises a cross-section selected from the group consisting of a circular shape, a non-symmetrical shape, a shape having irregular surfaces, a square shape, an oval shape, a rectangular shape, and a combination thereof.

6. The surgical space-making device of claim 1, wherein at least the secondary frame member comprises a cross-section selected from the group consisting of a circular shape, a non-symmetrical shape, a shape having irregular surfaces, a square shape, an oval shape, a rectangular shape, and a combination thereof.

7. The surgical space-making device of claim 1, wherein the first actuator comprises a rotary actuator or a linear actuator.

8. The surgical space-making device of claim 1, wherein the second actuator comprises a rotary actuator or a linear actuator.

9. The surgical space-making device of claim 1, wherein at least the second actuator is spring-biased to a locking position by a portion of the secondary frame member.

10. The surgical space-making device of claim 1, wherein the space-making frame is configured to expand asymmetrically about the axis upon selective advancement of the arcuate frame member and the secondary frame member.

11. The surgical space-making device of claim 1, wherein the interior lumen is sized to allow advancement of one or more medical instruments therethrough.

12. The surgical space-making device of claim 11, wherein the one or more medical instruments comprises at least an endoscope or an ablation device.

13. A surgical space-making device for separating anatomic structures to permit use of a medical device at a region of interest, the surgical space-making device comprising:

a handle having a first actuator and a second actuator, the first actuator and the second actuator independently operable relative to each other;

a shaft extending distally from the handle along an axis, the shaft having an interior lumen;

a working end at a distal end of the shaft where the interior lumen is open at the working end;

a space-making frame located at the working end, the space-making frame comprising a first arcuate frame member and a secondary frame member;

the first arcuate frame member comprising a first strut and a second strut and a mid-portion, where the first strut and the second strut are spaced apart at the working end and are mechanically coupled to the first actuator such that operation of the first actuator causes axial movement of the first arcuate frame member relative to the working end;

the secondary frame member having a first leg having a distal segment coupled to the mid-portion of the first arcuate frame member, a proximal segment of the secondary frame member coupled to the second actuator such that operation of the second actuator causes axial movement of the secondary frame member relative to the working end, wherein at least the first actuator is spring-biased to a locking position by a portion of the arcuate frame member;

wherein operation of the first actuator and the second actuator to move the first arcuate frame member and the secondary frame member in a single direction causes an axial movement of the space-making frame relative to the working end; and wherein operation of the first actuator and the second actuator to move the first arcuate frame member and the secondary frame member relative to each other causes the space-making frame to expand away in a radial direction from the axis of shaft to cause separation of tissue adjacent to the working end and creating a space at the region of interest such that the medical device can be advanced through the interior lumen to the region of interest.

14. The surgical space-making device of claim 13, wherein the space-making frame is compliant and configured such that an anatomical movement of an organ causes the space-making frame to deflect.

15. The surgical space-making device of claim 13, wherein the secondary frame member comprises a secondary arcuate frame member.

16. The surgical space-making device of claim 13, wherein the secondary frame member comprises a single strut.

17. The surgical space-making device of claim 13, wherein at least the first arcuate frame member comprises a cross-section selected from the group consisting of a circular shape, a non-symmetrical shape, a shape having irregular surfaces, a square shape, an oval shape, a rectangular shape, and a combination thereof.

18. The surgical space-making device of claim 13, wherein at least the secondary frame member comprises a cross-section selected from the group consisting of a circular shape, a non-symmetrical shape, a shape having irregular surfaces, a square shape, an oval shape, a rectangular shape, and a combination thereof.

19. The surgical space-making device of claim 13, wherein the first actuator comprises a rotary actuator or a linear actuator.

20. The surgical space-making device of claim 13, wherein the second actuator comprises a rotary actuator or a linear actuator.

21. The surgical space-making device of claim 13, wherein at least the second actuator is spring-biased to a locking position by a portion of the secondary frame member.

22. The surgical space-making device of claim 13, wherein the space-making frame is configured to expand asymmetrically about the axis upon selective advancement of the first arcuate frame member and the secondary frame member.

23. The surgical space-making device of claim 13, wherein the interior lumen is sized to allow advancement of one or more medical instruments therethrough.

24. The surgical space-making device of claim 23, wherein the one or more medical instruments comprises at least an endoscope or an ablation device.

* * * * *